US00PP17043P2

(12) United States Plant Patent
Yates

(10) Patent No.: US PP17,043 P2
(45) Date of Patent: Aug. 22, 2006

(54) ***ANTIRRHINUM* PLANT NAMED 'YACREY'**

(50) Latin Name: *Antirrhinum majus*
Varietal Denomination: YACREY

(76) Inventor: Frederic Yates, The Orchard, Holmes Chapel Rd., Somerford, Congleton, Cheshire CW12 45P (GB)

( * ) Notice: Subject to any disclaimer, the term of this patent is extended or adjusted under 35 U.S.C. 154(b) by 14 days.

(21) Appl. No.: 10/883,839

(22) Filed: Jul. 6, 2004

(51) Int. Cl.
*A01H 5/00* (2006.01)

(52) U.S. Cl. ..... Plt./322
(58) Field of Classification Search ..... Plt./322
See application file for complete search history.

*Primary Examiner*—Kent Bell

(57) ABSTRACT

A new cultivar of *Antirrhinum* plant named 'YACREY' that is characterized by rose and yellow flowers, mounding habit, and green foliage. In combination these traits set 'YACREY' apart from all other existing varieties of *Antirrhinums* known to the inventor.

2 Drawing Sheets

Genus: *Antirrhinum.*
Species: *majus.*
Denomination: 'YACREY'.

BACKGROUND OF THE INVENTION

The present invention relates to a new and distinct cultivar of snapdragon, known botanically as *Antirrhinum majus* and referred to hereinafter by the cultivar name 'YACREY'.

'YACREY' was selected by the inventor, in 2000, from a formal breeding program conducted in a cultivated area of Congleton, Cheshire, England. The breeding program was conducted by the inventor and established in 1990, the objective being to select cultivars of snapdragons that exhibit new flower colors along with new and improved growth habits. The inventor is also interested in producing varieties of snapdragon which do not set seed, since the seed setting on snapdragons is both unattractive and responsible for greatly reduced flowering.

'YACREY' is of hybrid origin and resulted from the induced cross-pollination of female and male parent seedlings. The female parent is a single plant which was raised from seed obtained from plants of the species *Antirrhinum majus* (unpatented) and the male parent is an unnamed seedling of *Antirrhinum* (unpatented) which the inventor held in his collection and which had arisen from previous open pollinations of *Antirrhinum* plants situated at the inventor's nursery. Whilst both parent plants exhibited a desirable semi-trailing habit, the inventor was hoping to find a hybrid with bright and unusual flower colors which would be sustained through the spring and early summer. 'YACREY' was selected for its combination of mounding habit and bright rose and yellow bicolored flowers that distinguish it from all other *Antirrhinum* known to the inventor. The closest comparison plants are the inventor's varieties of *Antirrhinum* known as 'Lemon Blush Chandelier' (unpatented) and 'Rose Pink Chandelier' (unpatented). 'YACREY' is distinguishable from the comparison plants by less trailing habit, and its rose and yellow flower colors.

The first asexual propagation of 'YACREY' was conducted in June 2000 by theinventor in Congleton, Cheshire, England. The method of propagation used was tip cuttings and the inventor has determined that 'YACREY' is stable and reproduces true to type in successive generations of asexual reproduction. The inventor has also determined that 'YACREY' is sterile and does produce a continual display of flowers through the main selling season for snapdragons.

SUMMARY OF THE INVENTION

The following traits have been repeatedly observed and represent the characteristics of the new *Antirrhinum* cultivar 'YACREY'. These traits in combination distinguish this cultivar from all other commercial varieties known to the inventor. 'YACREY' has not been tested under all possible conditions and phenotypic differences may be observed with variations in environmental, climatic, and cultural conditions.

1. *Antirrhinum* 'YACREY' exhibits a mounding habit.
2. *Antirrhinum* 'YACREY' exhibits short internodes.
3. *Antirrhinum* 'YACREY' exhibits rose and yellow flowers.
4. *Antirrhinum* 'YACREY' is propagated by tip cuttings.
5. *Antirrhinum* 'YACREY' is 25 cm. in height and 35 cm. in width at maturity.
6. *Antirrhinum* 'YACREY' is suitable for use as a container or patio plant.
7. *Antirrhinum* 'YACREY' is hardy to 10° Centigrade.
8. *Antirrhinum* 'YACREY' is sterile and floriferous.

BRIEF DESCRIPTION OF THE DRAWINGS

The accompanying color photographs illustrate the overall appearance of the new cultivar 'YACREY' showing the colors to be as true as is reasonably possible to obtain, in colored reproductions of this type. Colors in the photographs may differ from the color values cited in the detailed botanical description, which accurately describe the actual colors of the new variety 'YACREY'.

The drawing labeled as FIG. 1 illustrates the plant from a side perspective.

Figure 1:
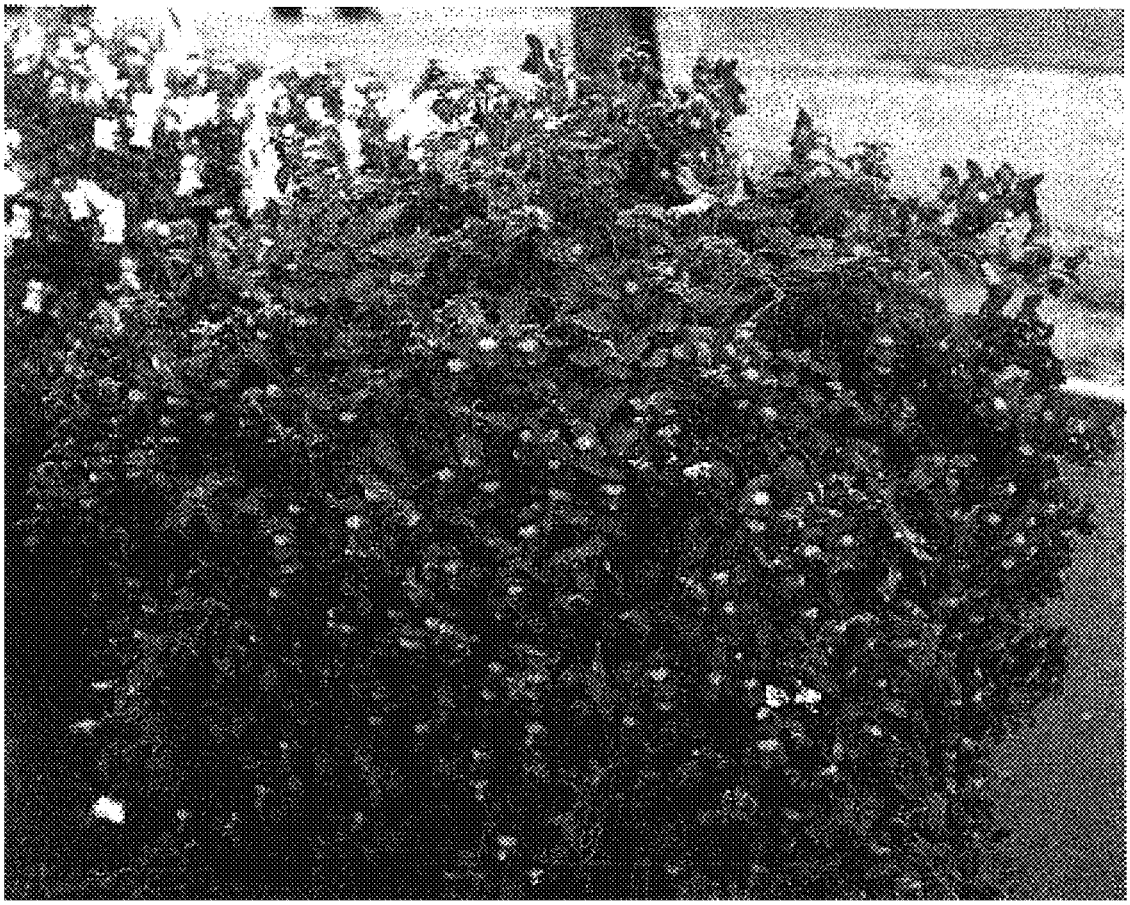
Figure 2:
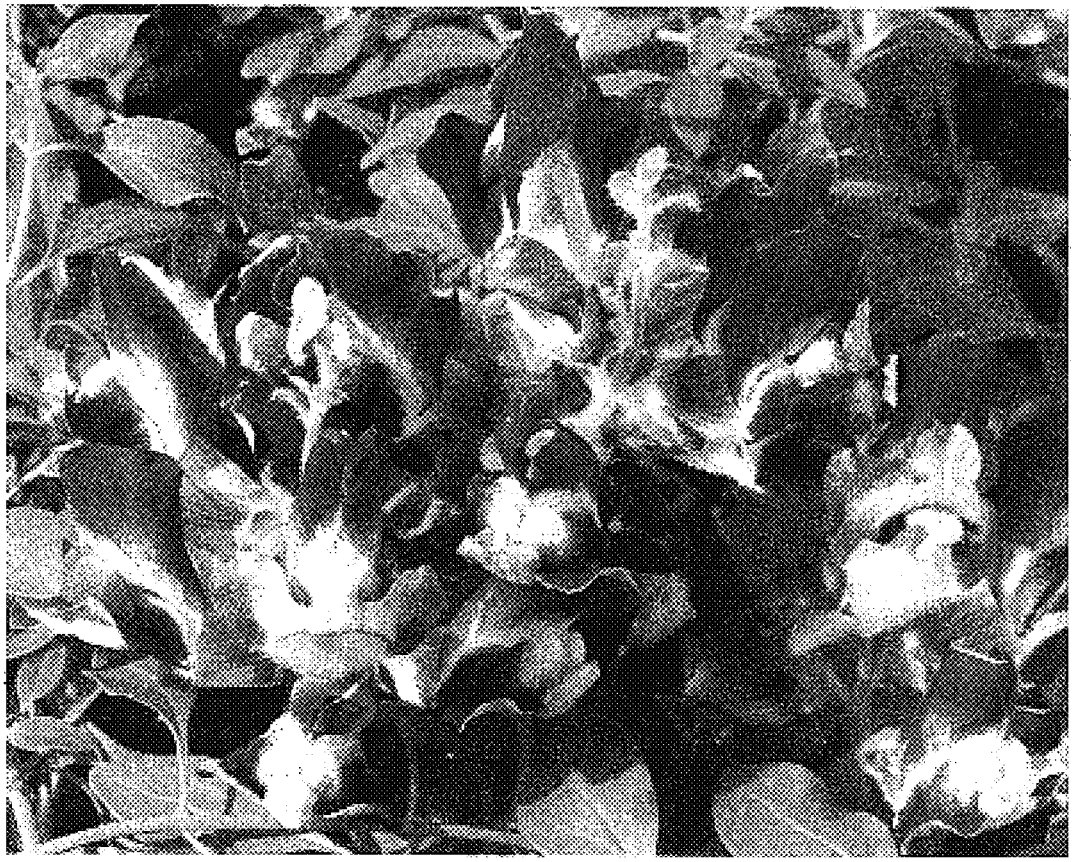

The drawing labeled as FIG. 2 illustrates a close-up view of the flower. The drawings are made using conventional photographic techniques and although foliage color may appear different from actual colors due to light reflectance, they are as accurate as possible by conventional photography.

BOTANICAL DESCRIPTION OF THE PLANT

The following is a detailed description of the new cultivar 'YACREY' as grown in a one-liter container under greenhouse conditions in Encinitas, Calif. Phenotypic differences may be observed with variations in environmental, climatic, and cultural conditions. The color determinations are in accordance with The Royal Horticultural Society except where general color terms of ordinary dictionary significance are used. There are no special growing requirements or growing problems known to the inventor.

Botanical classification: *Antirrhinum* 'YACREY'.
Species: *majus*.
Common name: Snapdragon.
Use: Container or patio plant.
Parentage: 'YACREY' is a hybrid plant that resulted from induced cross-pollination between the female and male parent plants. The male and female parents are unintroduced *Antirrhinum* hybrids from the inventors breeding program. Female parent plant: *Antirrhinum majus*. Male parent plant: Unnamed *Antirrhinum* hybrid.
- *Propagation.*—Tip cuttings.
- *Vigor.*—Vigorous.
- *Type.*—Annual.
- *Plant dimensions.*—15 cm. in height and 25 cm. in width in a one-liter container.
- *Production of flowers.*—An established single plant growing in a 2 gallon container or in a 10 inch hanging basket carries approximately 100 open flowers and a similar number of buds at any one time.
- *Root system.*—Fibrous.
- *Diseases and pests.*—No known pests or diseases.
- *Plant habit.*—Mounding.
- *Cropping time.*—8 weeks are needed to produce a finished 4-inch commercial container.
- *Time to develop roots.*—10 days are needed to develop roots on an initial cutting.
- *Temperature to develop roots.*—17–20° Centigrade.
- *Seasonal interest.*—Flowers in winter, spring and summer.
- *Hardiness.*—10° Centigrade.
- *Sunlight requirements.*—Normal.
- *Soil requirements.*—Free-draining nursery compost or peat.

Stem:
- *Stem shape.*—Cylindrical.
- *Stem color.*—144B.
- *Stem dimensions.*—15 cm in length by 2 mm in diameter.
- *Internode length.*—2 cm between nodes.
- *Stem surface.*—Stipitate glandular.
- *Branching habit.*—Basal branching.

Foliage:
- *Leaf arrangement.*—Opposite.
- *Leaf division.*—Simple.
- *Shape.*—Ovate.
- *Base.*—Cuneate.
- *Apex.*—Acute.
- *Venation pattern.*—Parallel.
- *Vein color* (*abaxial and adaxial surfaces*).—137C.
- *Margins.*—Entire.
- *Leaf surfaces* (*abaxial and adaxial*).—Lightly stipitate glandular.
- *Leaf color* (*adaxial surface*).—137A.
- *Leaf color* (*abaxial surface*).—137C.
- *Leaf dimensions* (*mature leaves*).—3.25 cm. in length and 1.50 cm in width.
- *Leaf dimensions* (*young leaves*).—1.25 cm. in length and 0.75 cm. in width.
- *Leaf fragrance.*—Grass-like.
- *Attachment.*—Petiolate.
- *Petiole dimensions* (*mature leaves*).—6 mm in length and 1.5 mm. in width.
- *Petiole dimensions* (*young leaves*).—4 mm. in length and 1 mm. in width.
- *Petiole color.*—137C.

Flower:
- *Inflorescence.*—Terminal raceme.
- *Aspect.*—Outward.
- *Flower shape.*—Bilabiate.
- *Flower dimensions.*—3 cm. in height, 3 cm. in depth and 1.50 cm. in width.
- *Flower color.*—72A, 4A and 72C are individually present on an individual flower.
- *Bud shape.*—Obovate.
- *Bud color.*—N78A.
- *Bud dimensions.*—1 cm. in length and 0.50 cm. in width.
- *Bud surface.*—Stipitate glandular.
- *Number of lips.*—Two.
- *Upper lip dimensions.*—1.50 cm. in length and 0.50 cm. in width.
- *Lower lip dimensions.*—1.50 cm. in length and 1.75 cm. in width.
- *Palate dimensions.*—1.50 cm. in width and 1.25 cm. in length.
- *Lobes* (*upper lip*).—Two lobes.
- *Lobes* (*lower lip*).—Three lobes.
- *Margins* (*upper lip*).—Revolute and ruffled.
- *Margins* (*lower lip*).—Slightly ruffled and spread.
- *Palate color* (*upper surface*).—Both 4A and 72A are individually present.
- *Palate color* (*lower surface*).—75D.
- *Upper lip color* (*adaxial surface*).—72A.
- *Upper lip color* (*abaxial surface*).—72C.
- *Lower lip color* (*adaxial surface*).—72A.
- *Lower lip color* (*abaxial surface*).—72C.
- *Corolla tube mouth.*—Closed.
- *Corolla tube color* (*inside surface*).—N155C.
- *Corolla tube color* (*outer surface*).—72C.
- *Corolla tube depth.*—1.50 cm. in depth.
- *Corolla tube diameter.*—0.4 mm.
- *Flowering season.*—Winter, spring and summer.
- *Flowering time.*—Diurnal.
- *Pedicel dimensions.*—4 mm. in length and 1 mm. in width.
- *Pedicel shape.*—Cylindrical.
- *Pedicel surface.*—Stipitate glandular.
- *Pedicel color.*—138C.
- *Calyx color.*—138B.
- *Number of sepals.*—Five sepals in number, fused at base.
- *Sepal color* (*adaxial and abaxial surfaces*).—138B.
- *Sepal surface.*—Stipitate glandular.
- *Sepal shape.*—Ovate.
- *Sepal dimensions.*—5 mm. in length and 3 mm. in width.
- *Sepal apex.*—Acute.
- *Sepal margin.*—Entire.
- *Flower fragrance.*—Slight fragrance.

Reproductive organs:

*Nectary surface* (*underside of palate*).—Lanate.

*Nectary color.*—2C.

*Stamens.*—4 in number.

*Stamen shape.*—Filament.

*Stamen color.*—N155C.

*Stamen dimensions.*—Two are 18 mm. in length and 0.75 mm. in width, and two are 15 mm. in length and 1 mm. in width.

*Anther dimensions.*—2 mm. in length and 1 mm. in width.

*Anther shape.*—Oval.

*Anther color.*—11 A.

*Quantity of pollen.*—Large amount.

*Color of pollen.*—11A.

*Pistil.*—One in number.

*Pistil color.*—72D.

*Pistil dimensions.*—15 mm. in length and 1 mm. in width.

*Pistil shape.*—Club shaped.

*Stigma dimensions.*—2 mm. in length and 1 mm. in width.

*Stigma color.*—138D.

*Ovary position.*—Superior.

*Ovary color.*—138D.

*Ovary shape.*—Globose.

*Ovary dimensions.*—2 mm. in length and 2 mm. in width.

*Ovary surface.*—Lanate.

Seed: No seed observed to date.

It is claimed:

1. A new and distinct cultivar of *Antirrhinum* plant named 'YACREY' as described and illustrated.

* * * * *